US00PP21872P2

(12) United States Plant Patent
Egger

(10) Patent No.: US PP21,872 P2
(45) Date of Patent: Apr. 12, 2011

(54) ***HEUCHERA* PLANT NAMED 'ELECTRIC LIME'**

(50) Latin Name: ***Heuchera* hybrid**
Varietal Denomination: Electric Lime

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 64 days.

(21) Appl. No.: 12/653,633

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell

(74) *Attorney, Agent, or Firm* — Klarquist Sparkman, LLP

(57) ABSTRACT

A new and distinct hybrid of *Heuchera* plant characterized by large, gold to lime colored leaves, red colored veins in cool temperatures, white flowers on a short flowering stems, excellent vigor, and excellent tolerance to heat and humidity.

2 Drawing Sheets

Botanical denomination: *Heuchera* hybrid.

Variety designation: 'Electric Lime'.

Cross Reference to sibling: *Heuchera* 'Electra' (U.S. Plant patent application Ser. No. 12/653,586).

BACKGROUND OF THE INVENTION

The present invention relates to a new and distinct cultivar of *Heuchera* hybrid and given the cultivar name of 'Electric Lime'. *Heuchera* is in the family Saxifragaceae. *Heuchera* 'Electric Lime' originated from a cross between *Heuchera* 'Southern Comfort' (U.S. Plant Pat. No. 20,364) as the seed parent, and *Heuchera* 426-2, a proprietary unreleased plant, as the pollen parent.

This new *Heuchera* is distinguished by:

1. large gold to lime colored leaves
2. red colored veins in cool temperatures,
3. white flowers on a short flowering stems,
4. excellent vigor,
5. excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old plant of *Heuchera* 'Electric Lime' in flower growing in a one gallon container in early spring in Canby, Oreg.

FIG. 2 shows a one-year-old plant in bloom in the garden in the summer.

FIG. 3 shows a one-year-old plant of the new variety in October in the garden in Canby, Oreg.

FIG. 4 shows a two year old plant in the summer that had been grown in the greenhouse in a one gallon container.

DETAILED PLANT DESCRIPTION

The following is a detailed description of the new *Heuchera* cultivar based on observations taken in May of a one-year-old specimen grown in a one gallon container in a cool greenhouse in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 1999 edition.

Plant:

*Form.*—Basal rosette, herbaceous perennial.
*Hardiness.*—USDA Zone 4 to 9.
*Size.*—14 cm tall from top of the foliage to the ground and 36 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Broadly ovate.
*Lobing/division.*—7 shallow lobes, the terminal is the longest.
*Venation.*—Palmate.
*Margins.*—Crenate.
*Apex.*—Mucronulate.
*Base.*—Cordate, lobes overlapping at the base.
*Blade size.*—11 to 14.5 cm long and 10 to 13 cm wide.
*Surface texture.*—Glandular on both sides.
*Petiole description.*—10 cm long and 2.5 mm wide, glandular hairs, Greyed Orange 172B.
*Leaf color.*—Variable depending amount of light, temperature, and age of the leaf; spring topside is a bright yellow green with red veins, between Yellow Green 151A and Yellow Green 152D with veins Greyed Orange 172A, bottom side closest to Yellow Green 152D; winter leaves are more lime, Yellow Green 146C with veins Greyed Orange 172A, bottom side closest to Green Yellow 147D tinted Greyed Purple 185A; summer leaves are lime with no red veins, Yellow Green 146C.

Inflorescence:

*Size.*—Grows to 16.5 cm long and 5.5 cm wide.

*Type.*—Thyrse.

*Number of flowers per thyrse.*—About 100 per thyrse.

*Number of thyrse.*—About 5 to 7 in spring bloom.

*Peduncle.*—Grows to 34 cm tall, 3 mm wide at base, Yellow Green 152A near the top and Grey Brown 199A near bottom, prominent glandular hairs, with no substantial cauline leaves.

*Pedicel.*—Variable in size, with glandular hairs, Yellow Green 151A.

*Bloom period.*—Late May to June in Canby, Oreg.

Flower bud:

*Size.*—1.5 mm wide and 2.5 mm long.

*Description.*—Glandular puberulent, ovoid.

*Color.*—White 155A on top half and Green Yellow 1D on bottom half.

Flower:

*Type.*—Perfect.

*Shape.*—Campanulate.

*Size.*—4 mm long and 5 mm wide.

*Petal description.*—5 in number, reflexed, 2 mm long, lanceolate, tip acute, margin entire, glabrous on both sides, White 155D on both sides.

*Calyx description.*—Campanulate, 4 mm long and 4 mm wide, with 5 lobes, divided ⅓ way to the base, glandular hairs on outside, glabrous inside; lobes inside and out White 155A except at tip Yellow Green 145C, acute, entire, Yellow Green 145D below lobes.

*Stamen description.*—5 in number, filaments 2 mm long, White 155D, anthers sterile, 0.5 mm, Greyed Yellow 160D.

*Pistil description.*—1, 2-beaked, 3.5 mm long, ovary 1.5 mm, Yellow Green 150C, style 2 mm long, Yellow Green 150D.

*Fragrance.*—None.

*Lastingness.*—Each thyrse blooms for about 2 weeks on the plant.

Fruit:

*Type.*—Two beaked capsule.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERA*

Compared to the seed parent, *Heuchera* 'Southern Comfort', the new hybrid has shorter flower stems and leaves that are lime green with red veins to lime rather than amber.

Compared to the pollen parent *Heuchera* 426-2, the new hybrid has larger leaves with stronger pubescence and lime to gold rather than green leaves.

Compared to *Heuchera* 'Tiramisu' (U.S. Plant Pat. No. 20,429), the new variety has much bigger leaves with red color in the veins rather than in and along the veins.

Compared to *Heuchera* 'Electra' (U.S. Plant patent application Ser. No. 12/653,586), the new variety has a much larger habit, bigger leaves, and red veins only in cool temperatures rather than year round.

I claim:

1. A new and distinct hybrid of *Heuchera* plant as herein illustrated and described.

* * * * *

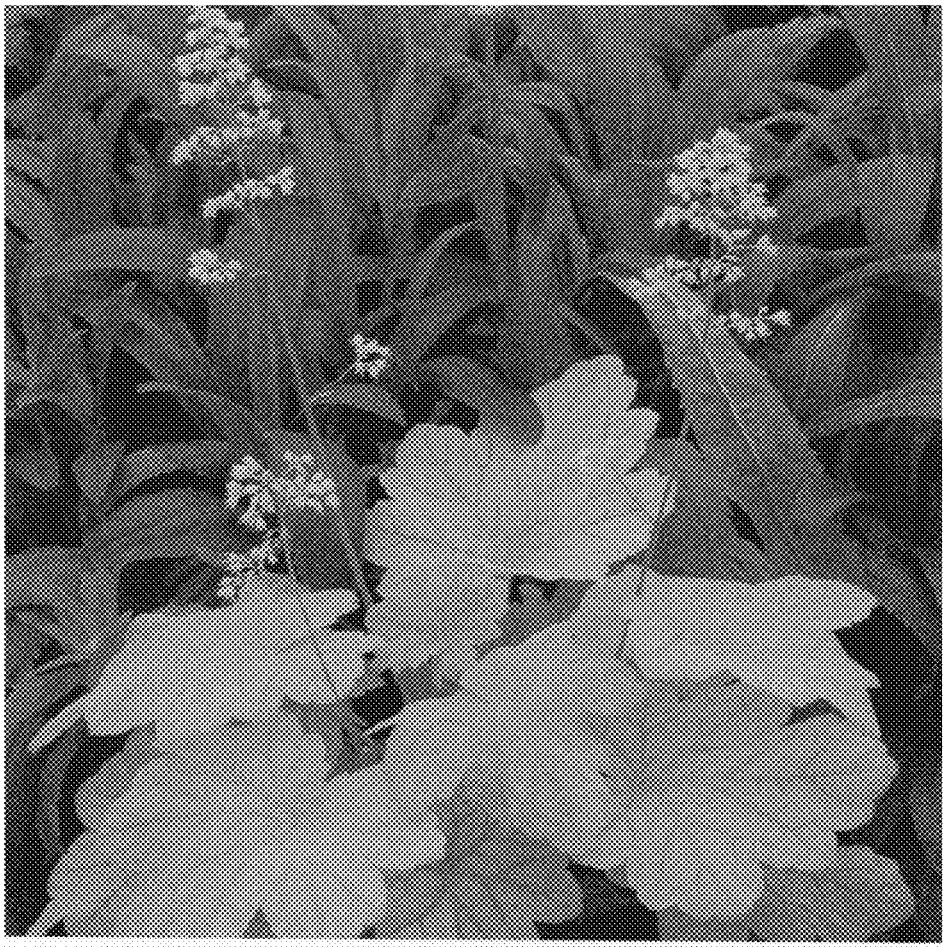
Figure 1 above, Figure 2 below
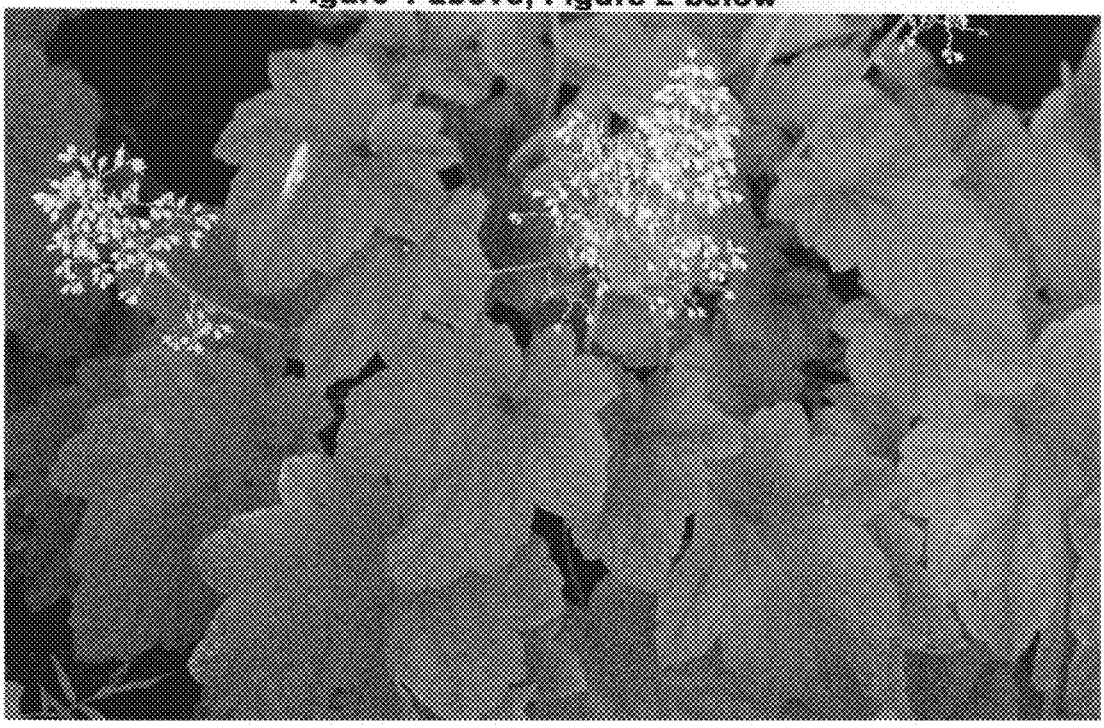

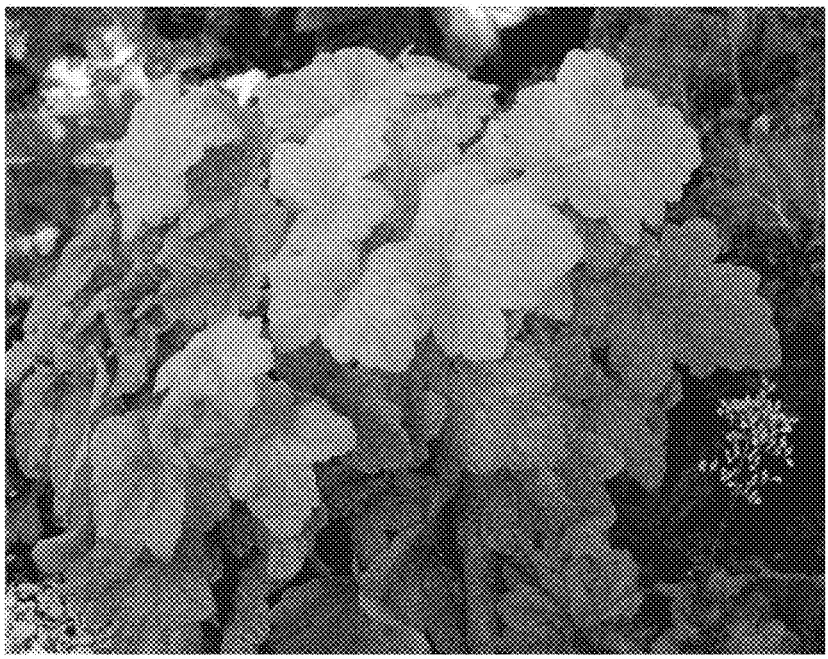

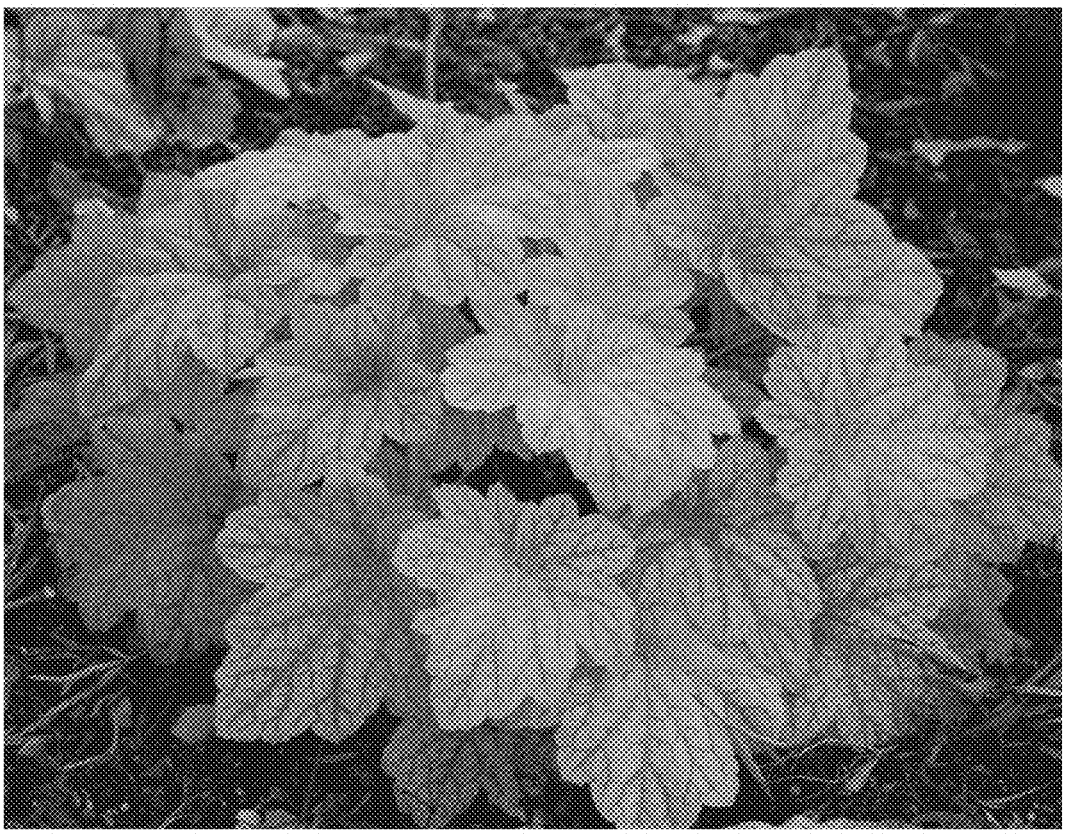
Figure 3 above, Figure 4 below